(12) United States Patent
Kotch

(10) Patent No.: US 10,603,459 B2
(45) Date of Patent: Mar. 31, 2020

(54) VARIABLE VISCOSITY VAPORIZER CARTRIDGE

(71) Applicant: Eric Kotch, Oakland, CA (US)

(72) Inventor: Eric Kotch, Oakland, CA (US)

( * ) Notice: Subject to any disclaimer, the term of this patent is extended or adjusted under 35 U.S.C. 154(b) by 318 days.

(21) Appl. No.: 15/723,885

(22) Filed: Oct. 3, 2017

(65) Prior Publication Data

US 2019/0022345 A1 Jan. 24, 2019

Related U.S. Application Data

(60) Provisional application No. 62/534,684, filed on Jul. 20, 2017.

(51) Int. Cl.
*A61M 16/14* (2006.01)
*A61M 16/10* (2006.01)
(Continued)

(52) U.S. Cl.
CPC ......... *A61M 16/145* (2014.02); *A24F 47/008* (2013.01); *A61M 11/042* (2014.02); *A61M 15/06* (2013.01); *A61M 16/109* (2014.02); *A61M 15/0021* (2014.02); *A61M 2205/0211* (2013.01); *A61M 2205/3653* (2013.01); *A61M 2205/3673* (2013.01); *A61M 2205/8206* (2013.01)

(58) Field of Classification Search
CPC .. A61M 11/00; A61M 11/041; A61M 11/042; A61M 11/08; A61M 15/00; A61M 15/0021; A61M 15/06; A61M 16/109; A61M 16/145; A24F 47/002; A24F 47/008

See application file for complete search history.

(56) References Cited

U.S. PATENT DOCUMENTS 8,955,522 B1 2/2015 Bowen et al.
9,078,474 B2 7/2015 Thompson
(Continued)

FOREIGN PATENT DOCUMENTS

EP 2805636 A2 11/2014
EP 3155908 A1 4/2017
(Continued)

*Primary Examiner* — Joseph D. Boecker
(74) *Attorney, Agent, or Firm* — NetLawyers LLP

(57) ABSTRACT

A vaporizer and vaporizer cartridge for inhaling vapors from vaporized oil. The vaporizer has a mouthpiece for use by a user to inhale the vapors. The mouthpiece is connected to a cartridge which contains the oil to be vaporized and the apparatus for vaporizing the oil. The vaporizer cartridge contains a reservoir of the oil which flows down to a wick, which is heated by a heating coil to a temperature necessary to vaporize the oil. Under the wick is a residue basin which collects any oil which fails to vaporize. The residue basin is placed at an optimal distance from the wick such that when the next user initiates another draw on the vaporizer, the un-vaporized oil in the residue basin is vaporized. Below the cartridge is a battery component that provides power to a heating coil which heats the wick to vaporize the oil. Air flows up from below the cartridge on one side, then cross-flows across the wick and residue basin, and up the other side of the cartridge to the mouthpiece.

14 Claims, 12 Drawing Sheets

(51) Int. Cl.
*A61M 15/06* (2006.01)
*A24F 47/00* (2020.01)
*A61M 15/00* (2006.01)
*A61M 11/04* (2006.01)

(56) References Cited

U.S. PATENT DOCUMENTS

| | | |
|---|---|---|
| 9,198,466 B2 | 12/2015 | Liu |
| 9,351,522 B2 | 5/2016 | Safari |
| 9,497,994 B2 | 11/2016 | Liu |
| 9,526,273 B2 | 12/2016 | Liu |
| 9,538,790 B2 | 1/2017 | Li |
| 9,549,573 B2 | 1/2017 | Monsees et al. |
| 9,555,203 B2 | 1/2017 | Terry et al. |
| 2009/0255534 A1 | 10/2009 | Paterno |
| 2013/0087160 A1 | 4/2013 | Gerghe |
| 2014/0007863 A1 | 1/2014 | Chen |
| 2014/0109921 A1 | 4/2014 | Chen |
| 2014/0123989 A1* | 5/2014 | LaMothe ............ A24F 47/008 131/328 |
| 2014/0261490 A1 | 9/2014 | Kane |
| 2015/0027457 A1 | 1/2015 | Janardhan et al. |
| 2015/0090279 A1 | 4/2015 | Chen |
| 2015/0128971 A1 | 5/2015 | Verleur et al. |
| 2015/0128976 A1 | 5/2015 | Verleur et al. |
| 2015/0146414 A1 | 6/2015 | Verleur et al. |
| 2015/0150306 A1 | 6/2015 | Chen |
| 2015/0164146 A1 | 6/2015 | Li et al. |
| 2015/0164147 A1 | 6/2015 | Verleur et al. |
| 2015/0272217 A1 | 10/2015 | Chen |
| 2015/0313284 A1 | 11/2015 | Liu |
| 2015/0313287 A1 | 11/2015 | Verleur et al. |
| 2015/0342257 A1 | 12/2015 | Chen |
| 2015/0342258 A1* | 12/2015 | Chen ................ H05B 3/06 131/329 |
| 2015/0359261 A1* | 12/2015 | Li .................. A24F 47/008 392/394 |
| 2016/0021934 A1 | 1/2016 | Cadieux et al. |
| 2016/0058073 A1 | 3/2016 | Chen |
| 2016/0073694 A1* | 3/2016 | Liu .................. H05B 3/40 131/329 |
| 2016/0121058 A1* | 5/2016 | Chen ................ A61M 11/04 |
| 2016/0219936 A1 | 8/2016 | Alarcon |
| 2016/0249682 A1 | 9/2016 | Leadley et al. |
| 2016/0262455 A1 | 9/2016 | Chen |
| 2016/0270447 A1 | 9/2016 | Borkovec |
| 2016/0278163 A1 | 9/2016 | Chen |
| 2016/0302487 A1 | 10/2016 | Chen |
| 2016/0366725 A1 | 12/2016 | Tucker et al. |
| 2017/0035110 A1 | 2/2017 | Keen |
| 2017/0035115 A1 | 2/2017 | Monsees et al. |
| 2017/0112193 A1 | 4/2017 | Chen |
| 2017/0164655 A1* | 6/2017 | Chen ................ A24F 47/008 |
| 2018/0070637 A1* | 3/2018 | Deng ................ A61M 15/06 |
| 2019/0046745 A1* | 2/2019 | Nettenstrom ........ A24F 47/008 |

FOREIGN PATENT DOCUMENTS

| | | |
|---|---|---|
| WO | 2015189613 A1 | 12/2015 |
| WO | 2016019353 A1 | 2/2016 |

* cited by examiner

VARIABLE VISCOSITY VAPORIZER CARTRIDGE

CROSS-REFERENCE TO RELATED APPLICATIONS

The present application claims the benefit of U.S. Provisional Application No. 62/534,684 filed on Jul. 20, 2017, incorporated by reference herein and for which benefit of the priority date is hereby claimed.

FEDERALLY SPONSORED RESEARCH

Not applicable.

SEQUENCE LISTING OR PROGRAM

Not applicable.

FIELD OF INVENTION

The present invention relates to a vaporizer, and more particularly to a vaporizer, cartomizer or cartridge which is configured to vaporize oils over a wide range of viscosities.

BACKGROUND OF THE INVENTION

Vaporizers are devices are used to vaporize an oil or other vaporizable material into a "vapor" for oral delivery to a user via inhalation. A vaporizer may include several elements, such as a power source, a reservoir containing the oil, and an atomizer to vaporize the oil. Vaporizers with an integrated atomizer and reservoir are referred to as a cartomizer. A vaporizer cartridge contains an integrated atomizer, reservoir and battery attachment assembly such that a power source such as a battery may be easily coupled to the battery attachment assembly to provide power to the vaporizer cartridge. The power source may be a battery attachment assembly attached to a battery. The vaporizer cartridge may include a reservoir for holding the oil and a heating coil with wick for vaporizing the oil to produce a vapor. The oil in the vaporizer cartridge may be consumed when the vaporizer generates a vapor in response to an adult user applying negative pressure to a mouthpiece of the vaporizer (e.g., an inhalation) which causes oil to be drawn to the wick.

All wicks have the disadvantage that they tend to leak and clog. Many vaporizers use a wick made of fiberglass with a nickel cadmium coil. Fiberglass wicks have the disadvantage that they easily clog if the oil has a high viscosity. Fiberglass wicks with nickel cadmium coils also have the disadvantage that they negatively impact the taste of the oil.

There has been a trend towards using ceramic wicks to address some of the disadvantages of fiberglass wicks. However, ceramic wicks have the disadvantage that they do not work well with high viscosity oil or oil of varying degrees of viscosity. Ceramic wicks work within a tight range of viscosity. Consequently, a particular ceramic wick would work only with an oil of a certain viscosity. If an oil of a different viscosity was desired, the user would have to use a different ceramic wick. The ceramic wick is porous, and oil will eventually flow down from the reservoir into the wick. One challenge is to make the oil flow down only when desired.

In order to prevent clogging the vaporizer, oils are treated with thinning agents to lower the viscosity as much as possible for fiberglass wicks, and significantly to whatever range is appropriate for the ceramic wick used. The most common thinning agents are vegetable glycerin ("VG", a sugar derived from plant oils), propylene glycol ("PG", a petroleum-based liquid) and polyethylene glycol ("PEG", a polymer of ethylene oxide). VG and PG are primarily used in the context of e-cigarettes, and PG and PEG are primarily used in the context of cannabis oils. Research shows that these substances may not be safe to use when they are inhaled as a vapor. When heated to temperatures that are commonly reached by vaporizers, VG, PG and PEG produce aerosols that contain carbonyls such as formaldehyde, acetaldehyde, and acrolein. The production and inhalation of compounds produced by heated thinning agents is problematic, as these compounds pose potential health risks. The International Agency for Research of Cancer (IARC) classifies formaldehyde as a Group 1 Agent, which is a compound that is known to be carcinogenic. The IARC classifies acetaldehyde as a Group 2B Agent, which is possibly carcinogenic to humans34 and similar to formaldehyde. Acrolein causes DNA damage and inhibits DNA repair, which suggests that it is a major determinant of lung cancer and lung carcinogenesis. (See, *Carbonyl Compounds Produced by Vaporizing Cannabis Oil Thinning Agents*, Troutt William D. and DiDonato Matthew D. The Journal of Alternative and Complementary Medicine. March 2017).

Thinning agents have the additional disadvantage in that they compromise the taste of the oil. Aside from the general negative impact on taste from the thinning agents, viscosity itself also impacts the taste of the oil. Generally speaking, higher viscosity oils tend to taste better than lower viscosity oils.

Even with the use of thinning agents, vaporizers tend to clog in response to variations in temperature and pressure. Such variations tend to push oil out of the reservoir into the wick. For example, when left in the car on a hot day, pressure in a closed container such as the vaporizer cartridge will build up, forcing the oil out of the reservoir and into the wick. Additionally, temperature will change the viscosity of the oil. In the case of a ceramic wick, any change of viscosity outside its range will affect its ability to vaporize the oil, and will potentially lead to clogging.

The addition of terpenes also affect the viscosity of oil. Terpenes have very low viscosity, and when added back into the extracted oil, changes the viscosity of oil. Unadulterated oil with have a viscosity of between 150 k cps to 300 k cps has a honey-like consistency. Adding a thinning agent such as PEG will bring the viscosity down to approximately 20 k cps, which would be required to work with a fiberglass wick. The viscosity of pre-extract terpenes is between 2 k-5 k cps. The pre-extract terpenes can be added to the oil to bring the overall viscosity down. The cartridge of the present invention can be used with oil with a viscosity between 15 k-50 k cps.

Attempts to use oils without thinning agents have resulted in high costs, problems and high return rates. Other attempts to address these problems are high end vertical wicks. One such solution has a vertical ceramic wick in a stainless steel housing and a glass tank. These have the disadvantage that they are very expensive, costing about 500% more than a ceramic wick.

There is a need for a vaporizer that works well with high viscosity oil or oils with different viscosity levels, does not require thinning agents, does not clog, and can be manufactured at a reasonable cost. Such a vaporizer allows use of 100% pure oil with no harmful additives, such as PG, VG or PEG. The present invention overcomes these limitations and provides other related advantages.

SUMMARY OF THE INVENTION

The present invention addresses the disadvantages of the need to use thinning agents to prevent clogging by providing for a residue basin in the vaporizer cartridge which collects any excess oil that it drawn to the wick. The residue basin sits directly below the wick. If excess oil is drawn the wick, but not vaporized on the draw or inhalation, the excess oil will drop into the residue basin and away from the wick, thereby preventing clogging. The residue basin is configured so the excess oil is in sufficiently close proximity to the wick that it is vaporized on the next draw or inhalation, thereby reducing waste and further potential clogging. The vaporization of the excess oil in the residue basin is further enhanced by a cross-draft across the wick created by configuring the air intake vents and vapor channel on opposite sides of the housing.

In one embodiment of the present invention, the vaporizer cartridge comprises a housing or shell, which may be made of plastic, clear plastic, glass or other like material. The housing is elongate, and generally would be cylindrical in shape. Within the top portion of the housing is a reservoir configured to hold the vaporizable material. Below the reservoir is a vapor assembly which comprises a wick with a heating coil wrapped around and attached to a power source or battery component, and a residue basin situated below the wick. The residue basin is configured to be at such a depth that when oil is not vaporized on the wick, the resulting oil residue will fall into the residue basin and will be vaporized on the next draw of the vaporizer. In one embodiment, the residue basin extends down between two millimeters and five millimeters from the wick. In one embodiment of the present invention, a lower air channel extends from bottom of the housing up to said wick, and an upper air channel extends from top of the housing down to the wick, and a cross air channel extends from top of the lower air channel across the wick and over the residue basin to the bottom of the upper air channel. In one embodiment of the invention, the wick is made of ceramic. In embodiment of the invention, the residue basin is made of silicone. In one embodiment of the present invention, the vapor assembly comprises an upper assembly and a lower assembly, wherein the upper assembly comprises an upper assembly base, at least one oil vent, at least one oil feeder tube, and two wick retainers, and the lower assembly comprises a lower assembly base, two wick receptacles, a lower assembly air channel delimiter, and the residue basin. The upper assembly is situated on top of the lower assembly such that said wick is held in place by the wick retainers and the wick receptacles. In one embodiment of the present invention, the upper assembly has a support made of material that is more rigid than the upper assembly. The support is situated in a depression on top of the upper assembly, and provides structural support for the upper assembly, and which also gives it a more secure fit within the housing. In another embodiment of the present invention, a vaporizer capable of vaporizing oils with different viscosity characteristics comprises the vaporizer cartridge, a mouthpiece and a battery component for providing power to the heating coil.

In one embodiment of the present invention, the vaporizer cartridge comprises a mouthpiece, a housing, an upper assembly, a lower assembly, and a battery attachment assembly. The mouthpiece is used by the user to apply negative pressure to the vaporizer. The mouthpiece is connected to the housing, which in one embodiment is a cylindrical tube of transparent plastic. The top of the housing has a vapor outflow vent and an oil insertion vent. A vapor channel delimiter affixed to the top of the housing extends approximately two-thirds the way down the housing. The vapor channel delimiter is affixed offset from the center of the interior of the housing such that the vapor channel delimited thereby is a minority of the area circumscribed, and provides a channel out through the vapor outflow vent. The majority of the area circumscribed comprises the reservoir which is filled with oil through the oil insertion vent. After the reservoir has been filled, the oil insertion vent is plugged with a cap. The remaining approximately one-third of the housing serves to accommodate the upper assembly and the lower assembly.

From a top view, the upper assembly is semi-circular in shape such that when inserted into the housing, the truncated edge of the semi-circle abuts the bottom of the vapor channel delimiter, thereby providing a seal for the bottom of the reservoir and leaving the vapor channel unimpeded. The upper assembly is comprised of an upper assembly base and an upper assembly support. The upper assembly base is made of a semi-flexible material such as silicone in which the top portion has an indentation covering a majority of the semi-circle into which the upper assembly support fits. The upper assembly support is a small plastic or polycarbonate semi-circular piece that fits into the indentation at the top of the upper assembly base and makes the base more rigid, thereby reducing leakage from the reservoir. Originally, the upper assembly was just silicone, but under variable temperature and pressure, the shape would deform and oil would leak down the side. It was discovered that the addition of the upper assembly support as a stabilizer would maintain the internal form structure at all times. The upper assembly support provided the further advantage that it created a good seal. Originally tried a metal plate on top, that but didn't keep the structure and created a pressure issue. The upper assembly base has two upper assembly wick retainers extending down from the semi-circle with notches on the end. The notches set on top of a cylindrical ceramic wick which is mounted on the lower assembly. The upper assembly wick retainers each have an upper assembly oil feeder tube extending from the semi-circle down through the notches. In one embodiment of the present invention, the upper assembly oil feeder tubes are 0.8 mm diameter. Generally, one orders a cartridge tuned for a specific viscosity which is determined by the size of the tubes which allow oil of a certain viscosity to flow down. However, this has the disadvantage that it allows to much oil to seep through to the wick, causing clogging. Most oil on market is low viscosity at around 10 k cps. Consequently, vaporizers can have a standard size wick and cartridge configuration because that is tuned for standard viscosity. However, such low viscosity oil tends to seep down through to the wick, and a higher viscosity oil is too thick to get down the holes. In the present invention, heat from heating coil heats the upper assembly oil feeder tube and brings down oil; as opposed to different size hole for different viscosity bringing oil down to wick. Instead of tubes coming down side where no heat goes up tubes, the upper assembly oil feeder tubes go directly up into the oil. The semi-circle also has two upper assembly retaining lip receptacles which accept the two upper assembly support retaining lips on the upper assembly support, thereby providing a more secure connection. The upper assembly support also has to upper assembly oil vents which are positioned directly over the upper assembly oil feeder tubes, thereby allowing oil to flow from the reservoir, through the upper assembly oil vents, and through the upper assembly oil feeder tubes to the wick for vaporization.

The lower assembly is comprised of the lower assembly base, a wick and a heating coil. The lower assembly base is made from a semi-flexible material such as silicone. From the top view, the lower assembly base is circular in shape and fits snugly in the housing below the upper assembly. The lower assembly base is cylindrical in shape and is generally hollow. Extending from the bottom of the upper assembly base is a lower assembly air channel delimiter. The air channel delimiter is affixed offset from the center of the lower assembly base such that the air channel delimited thereby is a minority of the area circumscribed and the bottom of that area is open and provides a lower assembly air channel. From the bottom, the majority of the area circumscribed comprises the lower assembly residue basin floor. From the top, the area circumscribed by the walls of the lower assembly base and lower assembly air channel delimiter circumscribe the lower assembly residue basin. Before discovering that the lower assembly residue basin was an optimal feature for vaporizing oil, a nano cloth was tried. However, it was found the nano cloth got saturated and the captured oil was not able to be vaporized. The oil tended to bead off and flow away.

At the top of the walls of the lower assembly base are two wick receptacles which are positioned such that the wick is positioned directly over the lower assembly residue basin. The wick comprising a ceramic rod sits on top of the lower assembly. A nick cadmium wire wraps around the wick with the ends, referred to as legs, extending down through the lower assembly such that they contact the battery attachment assembly. Originally, a hollow ceramic wick was used. However, a hollow wick tended to hold excess oil, seeped down and clogged. It was discovered that a solid ceramic wick avoided these disadvantages. The base of the lower assembly is made of silicone, and the legs can be pushed through the silicone to come into contact with the battery assembly. This provides a tight seal around the legs. The legs of the heating coil pass go through the lower assembly residue basin floor. There are no holes tooled in the silicone; the legs are pushed through the silicone when assembled. This prevents leakage from the lower assembly residue basin. This also serves to secure the wick to the lower assembly and conduct electricity to the heating coil from the battery which is in contact with the battery attachment assembly. The proximal end of the wire extends up from the proximal side of the battery attachment assembly, through the lower assembly and wraps 5 times around the wick, and then extends down through the distal side of the lower assembly and contacts the distal side of the battery attachment assembly. The lower assembly also has an air channel on the distal side. The heating coil is wrapped around the wick with each leg extending down through the lower assembly residue basin floor where it is electrically connected to the battery attachment assembly. When the lower assembly is inserted into the housing, it is positioned such that the wick is seated in the upper assembly wick retainers and the lower assembly air channel is on the opposite side as the vapor channel.

The battery attachment assembly is cylindrical in shape and partially fits in the housing securely under the lower assembly creating a sealed cartridge. It serves as the interface between the lower assembly and the battery. The battery attachment assembly has a retainer, a center pin, and an air intake vent. The legs of the heating coil are held in place between the rim and retainer by pressure from the retainer. A battery attachment assembly comprising a battery housing and a battery is secured to the battery attachment assembly, thereby completing the vaporizer. The battery is positioned inside the battery housing such that it comes into contact with the center pin, thereby providing electrical power to the heating coil.

When a user inhales through the mouthpiece, negative pressure is created within the vaporizer cartridge. The negative pressure causes air to be pulled through the battery where it triggers a sensor that causes a battery attached via the battery attachment assembly to provide electrical power to the heating coil, which heats the wick. When the wick is heated, heat is released up through the upper assembly oil feeder tubes. The oil in proximity to the upper assembly oil feeder tubes becomes less viscous, and flows down through the upper assembly oil feeder tubes into the lower assembly residue basin where it is vaporized by the heat generated from the wick. The lower assembly residue basin is deep enough so that it can capture oil that have previously leaked through the upper assembly oil feeder tubes, but is also shallow enough so that any captured oil will be vaporized on the next heat cycle of the wick. This advantageously collects enough residue to vaporize without clogging. The negative pressure causes air to be pulled in through the air intake vent in the battery attachment assembly, up through the lower assembly air channel, across the wick and over the lower assembly residue basin, thereby pulling the vapor up past the upper assembly, through the vapor channel, out of the vapor outflow vent of the housing and through the mouthpiece to the user. It was discovered that the cross-draft across the wick advantageously captured more vapor than a straight draw.

BRIEF DESCRIPTION OF THE DRAWINGS

A complete understanding of the present invention may be obtained by reference to the accompanying drawings, when considered in conjunction with the subsequent, detailed description.

DETAILED DESCRIPTION

Before the invention is described in further detail, it is to be understood that the invention is not limited to the particular embodiments described, as such may, of course, vary. It is also to be understood that the terminology used herein is for the purpose of describing particular embodiments only, and not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed with the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, if dates of publication are provided, they may be different from the actual publication dates and may need to be confirmed independently.

Figure 1:
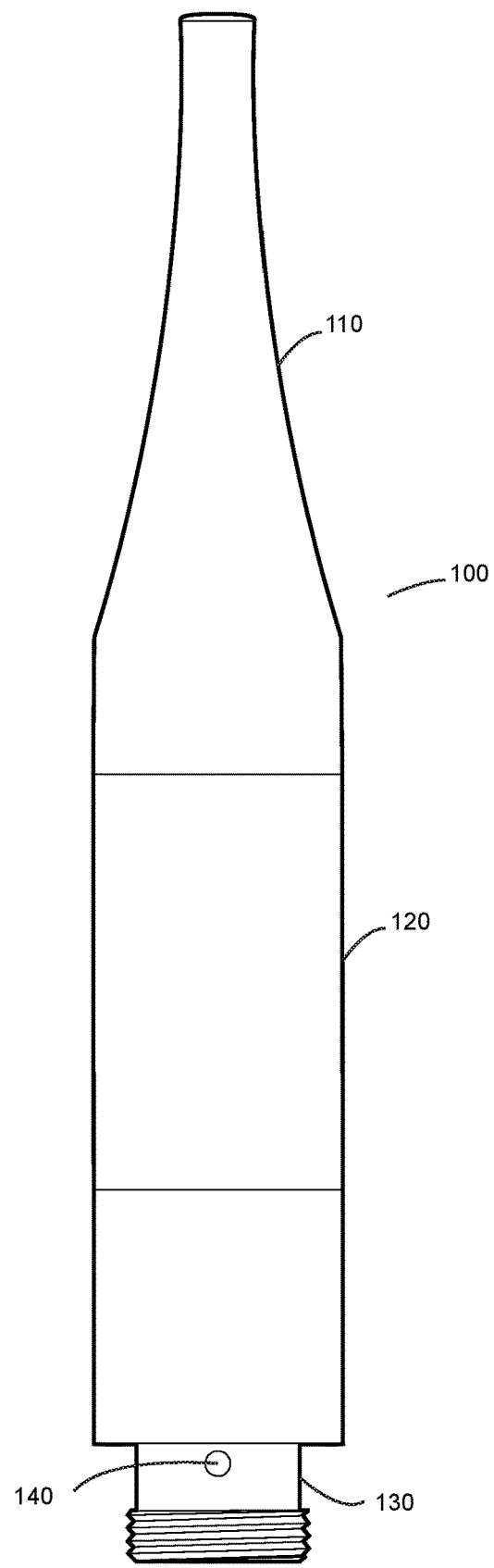
FIG. 1 is a side view diagram of an assembled vaporizer cartridge.

FIG. 1 shows a side view of an assembled vaporizer cartridge 100. The vaporizer cartridge 100 comprises a mouthpiece 110, a housing 120, and a battery attachment assembly 130 with an air intake vent 140. The mouthpiece 110 is used by the user to apply negative pressure to the vaporizer cartridge 100. The mouthpiece 110 is connected to the housing 120, which in one embodiment the housing 120 is a cylindrical tube of transparent plastic. The battery attachment assembly 130 is attached to the bottom of the housing 120. In one embodiment, the battery attachment assembly 130 is made of metal or similar rigid material and is configured so that the top cylindrical portion has a diameter slightly less than the diameter of the housing 120 such that the top portion of the battery attachment assembly 130 slides securely into the housing 120. In one embodiment, the battery attachment assembly 130 has a lower portion below the air intake vent 140 containing threads such that the battery attachment assembly can be screwed onto a battery housing containing a battery. Other methods of attaching the battery attachment assembly 130 to a power source can be used, such as using lips and creases to create a snap connection.

Figure 2:
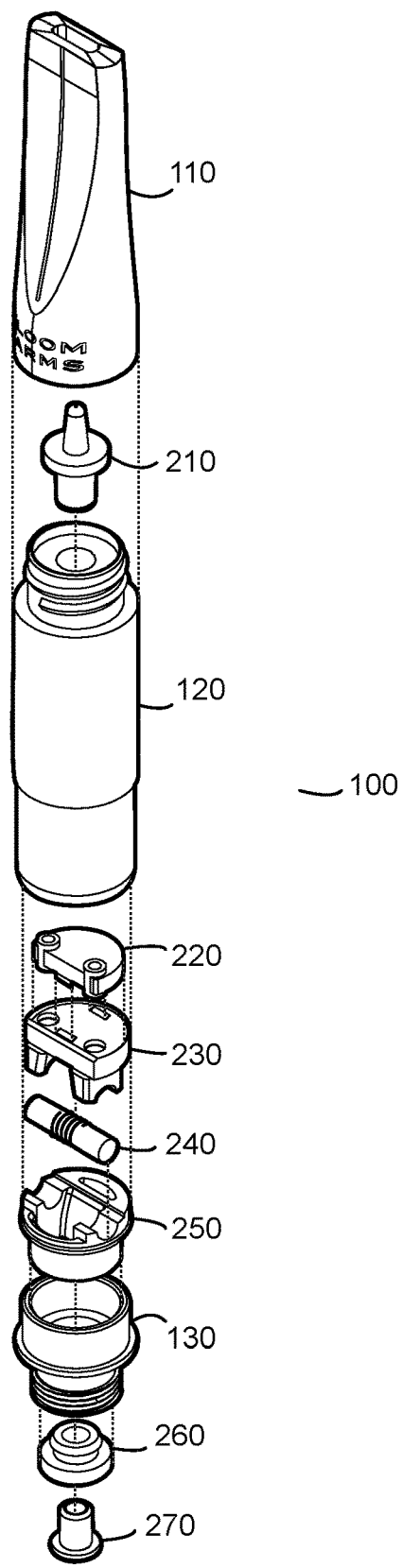
FIG. 2 is an oblique side view exploded diagram of a vaporizer cartridge.

FIG. 2 shows a side view of the vaporizer cartridge 100 exploded. Starting from the top, shown is the mouthpiece 110. The mouthpiece 110 is connected to the housing 120 by screwing on the threads at the top of the housing 110. A cap 210 is used to seal the top of the housing 120 after the reservoir portion of the housing 120 has been filled with oil. Contained within the bottom portion of the housing 110 are the upper assembly comprising the upper assembly support 220 and upper assembly base 230, and the lower assembly comprising the wick 240 and lower assembly base 250. The bottom of the housing 120 is sealed by the battery attachment assembly 130 with a retainer 260 and center pin 270.

Figure 3:
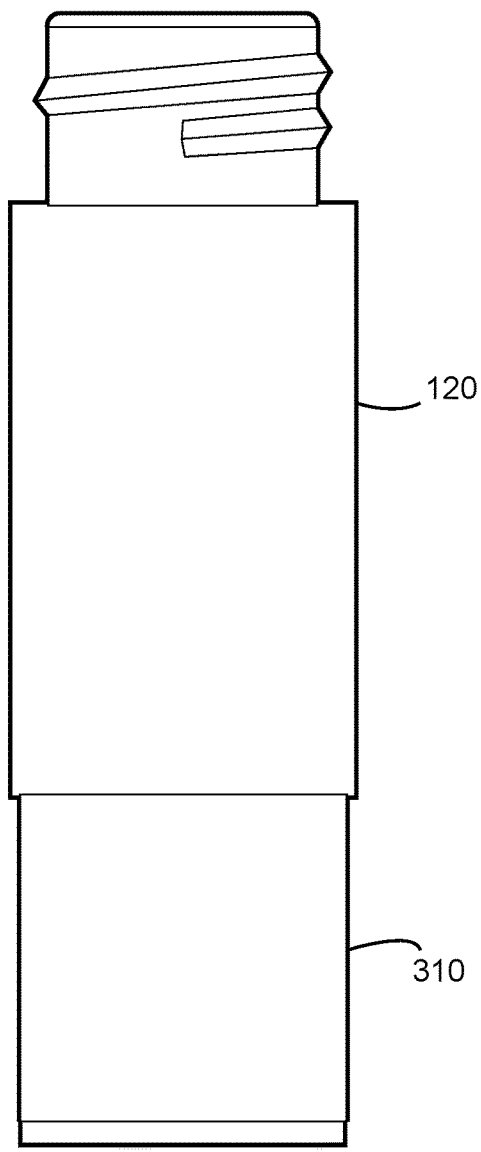
FIG. 3 is a side view diagram of the housing of a vaporizer cartridge.

Turning now to FIG. 3, shown is a side view of the housing 120. The assembly space 310 is the lower portion of the housing 120 into which the upper assembly, lower assembly and portion of the battery attachment assembly are housing. The upper portion of the housing is the reservoir containing the oil. The threads at the top of the housing are used to secure the housing 120 to the mouthpiece.

Figure 4:
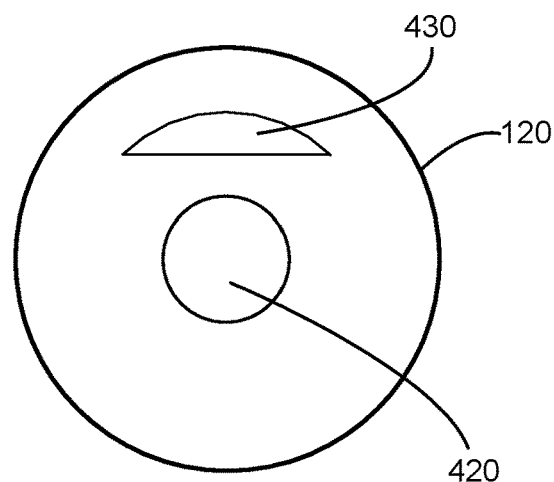
FIG. 4 is a top view diagram of the housing of a vaporizer cartridge.

Turning now to FIG. 4, shown is a top view of the housing 120. The top of the housing 120 has a vapor outflow vent 430 and an oil insertion vent 420.

Figure 5:
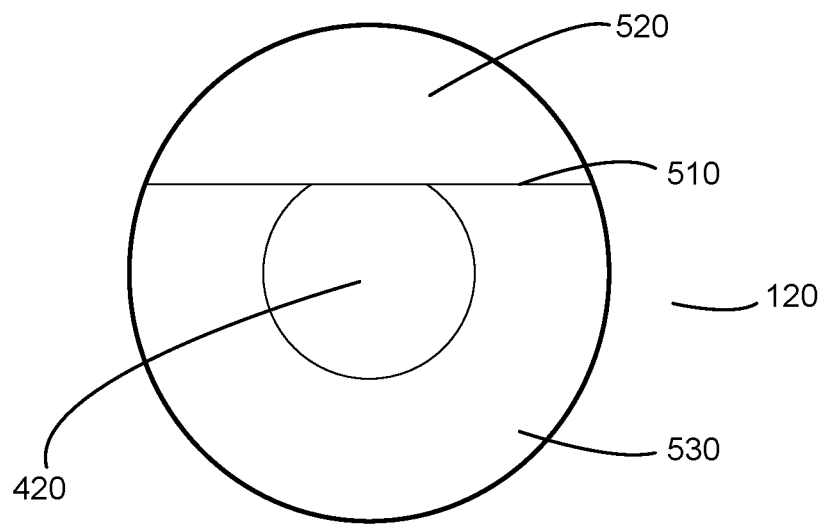
FIG. 5 is a bottom view diagram of the housing of a vaporizer cartridge.

Turning now to FIG. 5, shown is a bottom view of the housing 120. A vapor channel delimiter 510 affixed to the top of the housing 120 extends approximately two-thirds the way down the housing 120 to the assembly space. The vapor channel delimiter 510 is affixed offset from the center of the interior of the housing 120 such that the vapor channel 520 delimited thereby is a minority of the area circumscribed, and provides a vapor channel 520 out through the vapor outflow vent 430. The majority of the area circumscribed comprises the reservoir 530 which is filled with oil through the oil insertion vent 420. After the reservoir 530 has been filled, the oil insertion vent 420 is plugged with a cap 210.

Figure 6:
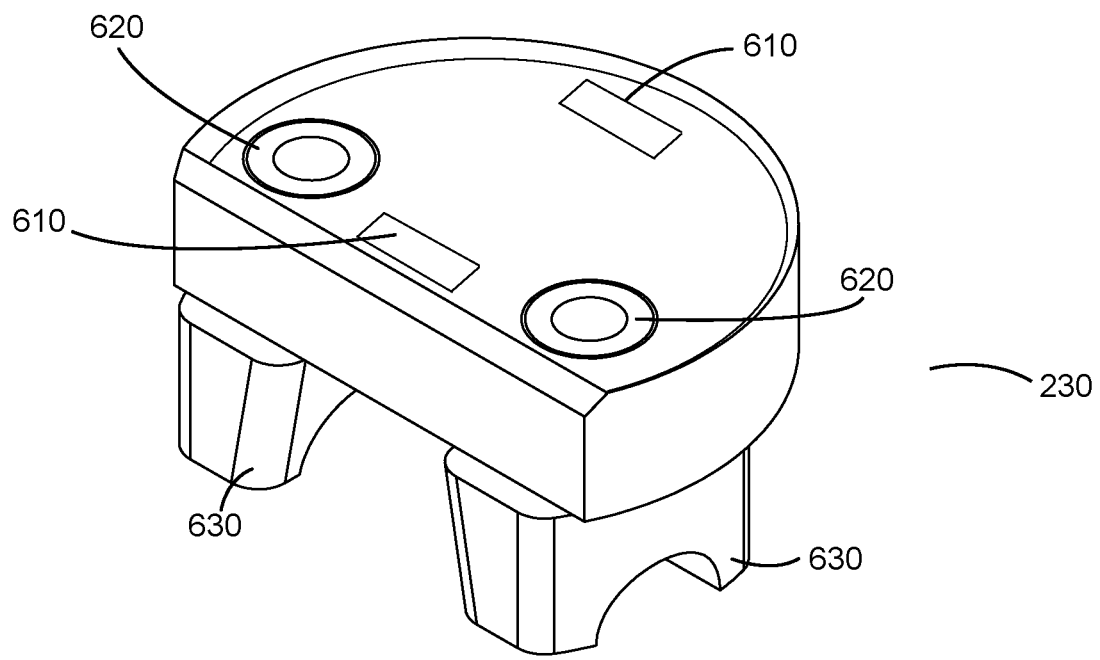
FIG. 6 is an oblique side view diagram of the upper assembly base.

Turning now to FIG. 6, shown is a top oblique view of the upper assembly base 230. At the top of the upper assembly base 230 are two upper assembly retaining lip receptacles 610 which are used to accept upper assembly support retaining lips, thereby securing the upper assembly support to the upper assembly base 230. Also at the top of the upper assembly base 230 are two upper assembly oil feeder tubes 620 which extend down through each of the upper assembly wick retainers 630.

Figure 7:
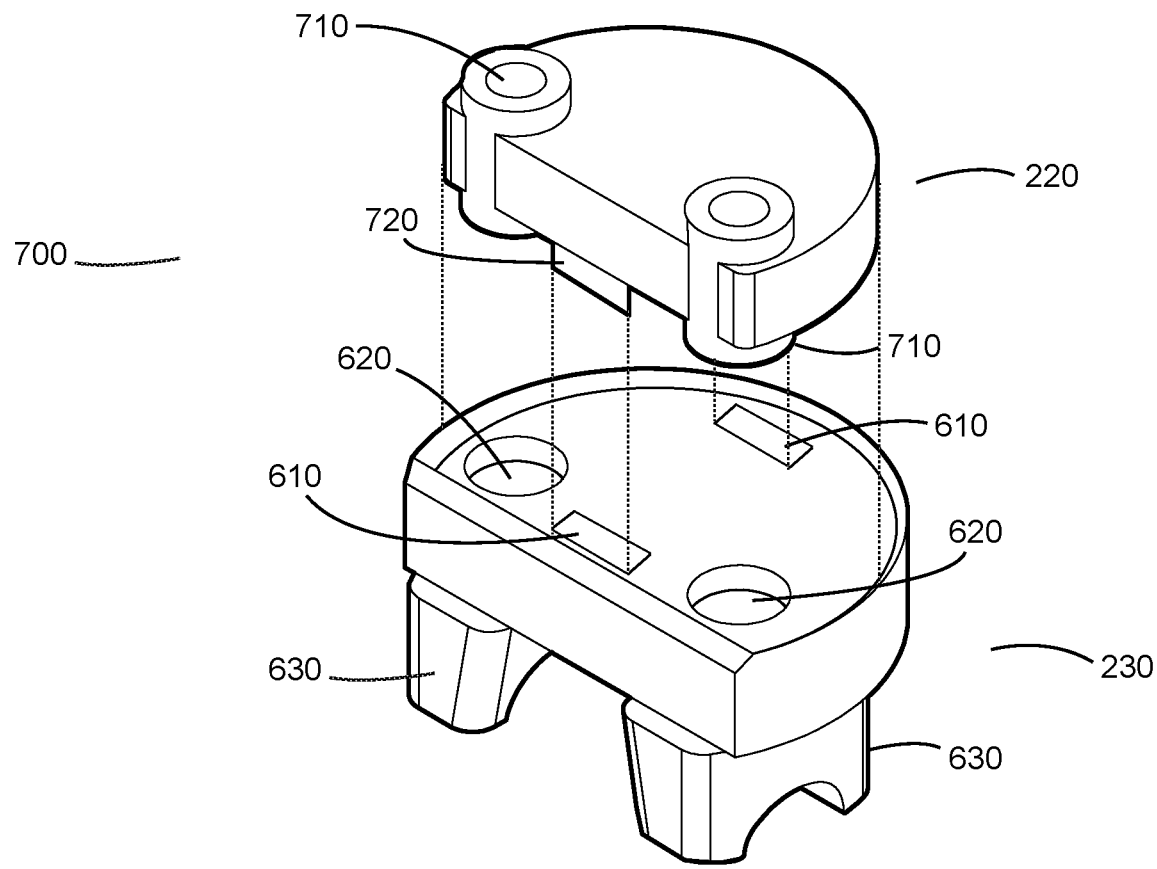
FIG. 7 is an oblique side view exploded diagram of the upper assembly.

Turning now to FIG. 7, shown is the upper assembly 700 which is comprised of the upper assembly base 230 and upper assembly support 220. The upper assembly support 220 has two upper assembly oil vents 710 which interface with the two upper assembly oil feeder tubes 620 of the upper assembly base 230. In one embodiment of the present invention, the upper assembly oil feeder tubes 620 are 0.8 mm diameter. When the a draw is initiated in the vaporizer, the wick is heated and oil proximal to the upper assembly support oil vents 710 is warmed thereby facilitating its flow through the upper assembly support oil vents 710 down through the upper assembly oil feeder tubes 620 for vaporization in the lower assembly oil residue basin. The upper assembly support 220 also has two (one of which is shown) upper assembly support retaining lips 720 which fit into the two upper assembly support retaining lip receptacles 610 on the upper assembly base 230, thereby securing the upper assembly support 220 to the upper assembly base 230.

Continuing with FIG. 7, the upper assembly 700 is semi-circular in shape such that when inserted into the housing, the truncated edge of the semi-circle abuts the bottom of the vapor channel delimiter, thereby providing a seal for the bottom of the reservoir and leaving the vapor channel unimpeded. The upper assembly base 230 is made of a semi-flexible material such as silicone in which the top portion has an indentation covering a majority of the semi-circle into which the upper assembly support 220 fits. The upper assembly support 220 is a small plastic semi-circular piece that fits into the indentation at the top of the upper assembly base 230 and makes the base more rigid, thereby reducing leakage from the reservoir. The upper assembly base 230 has two upper assembly wick retainers 630 extending down from the semi-circle with notches on the end. The notches set on top of a cylindrical ceramic wick which is mounted on the lower assembly. The upper assembly wick retainers 630 each have an upper assembly oil feeder tube 620 extending from the semi-circle down through the notches. The semi-circle also has two upper assembly retaining lip receptacles 610 which accept the two upper assembly support retaining lips 720 on the upper assembly support 220, thereby providing a more secure connection. The upper assembly support 220 also has two upper assembly oil vents 710 which are positioned directly over the upper assembly oil feeder tubes 720, thereby allowing oil to flow from the reservoir, through the upper assembly oil vents, 710 and through the upper assembly oil feeder tubes 620 to the wick and lower assembly residue basin for vaporization.

Figure 8:
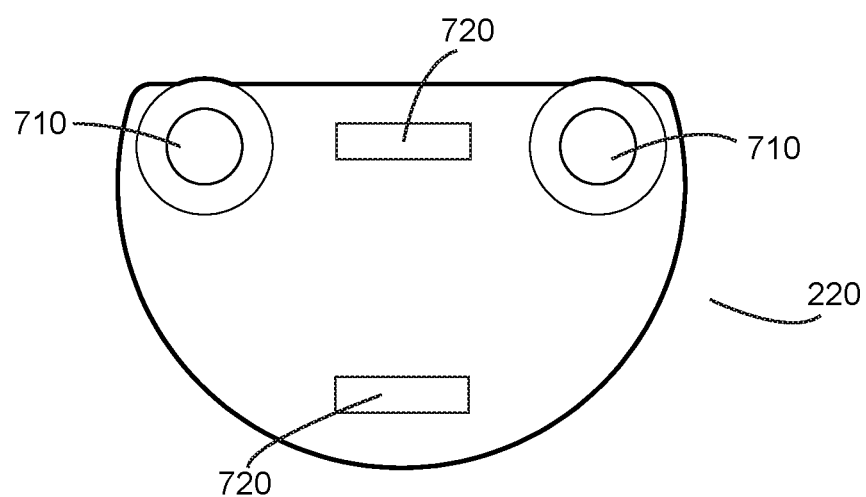
FIG. 8 is a bottom view diagram of the upper assembly support.

Turning now to FIG. 8, shown is a bottom view of the upper assembly support 220. The upper assembly support 220 has two upper assembly oil vents 710 which interface with the two upper assembly oil feeder tubes of the upper assembly base. The upper assembly support 220 also has two upper assembly support retaining lips 720 which fit into the two upper assembly support retaining lip receptacles on the upper assembly base, thereby securing the upper assembly support 220 to the upper assembly base.

Figure 9:
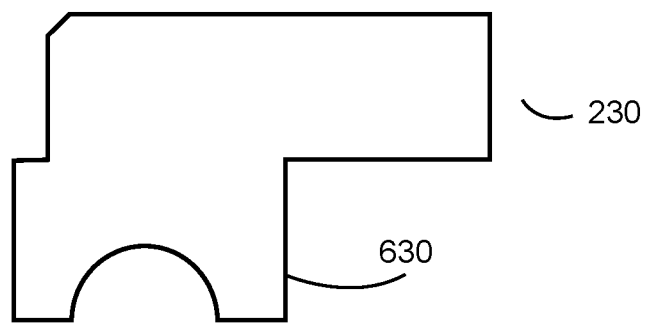
FIG. 9 is a side view diagram of the upper assembly base.

Turning now to FIG. 9, shown is a side view of the upper assembly base 230 showing the upper assembly wick retainer 630 extending down. The semi-circular notch of the upper assembly wick retainer 630 sits atop the wick upon which oil flows down through the upper assembly oil feeder tubes inside each upper assembly wick retainer 630.

Figure 10:
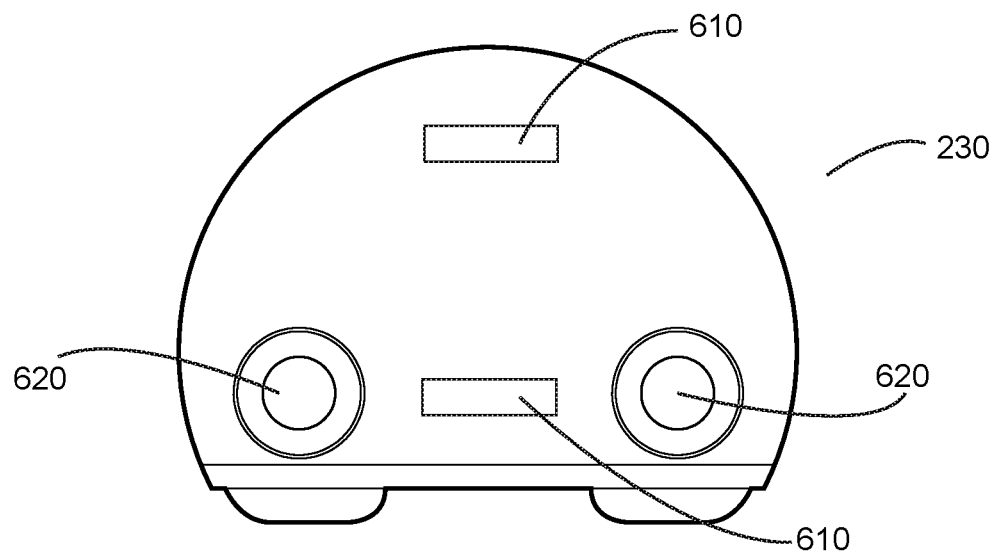
FIG. 10 is a top view diagram of the upper assembly base.

Turning now to FIG. 10, shown is a top view of the upper assembly base 230. When the upper assembly support is placed on top of the upper assembly base 230, the two upper assembly oil vents interface with the two upper assembly oil feeder tubes 620 of the upper assembly base 230. The upper assembly support retaining lips which fit into the two upper assembly support retaining lip receptacles 610 on the upper assembly base 230, thereby securing the upper assembly support to the upper assembly base 230.

Figure 11:
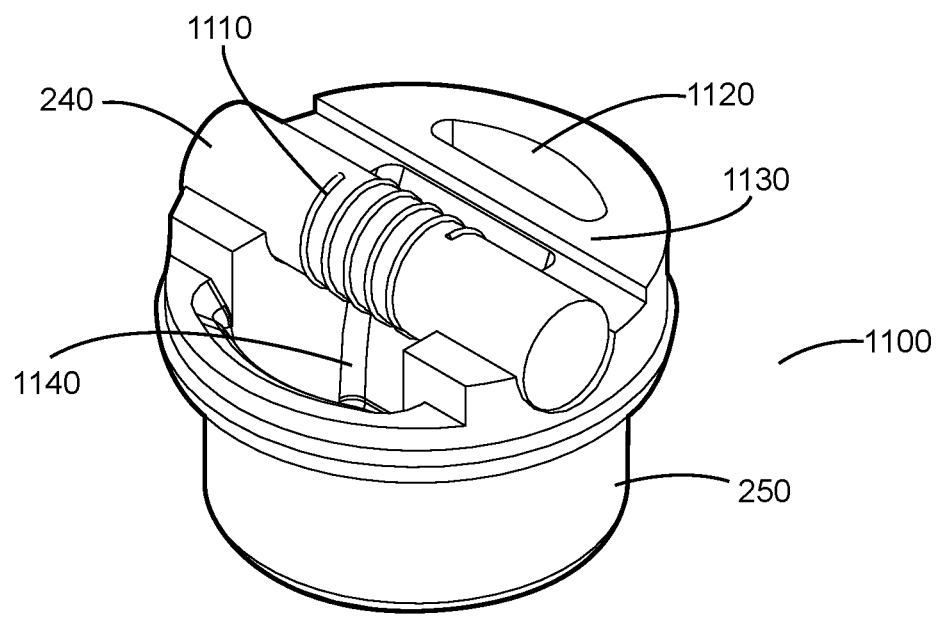
FIG. 11 is an oblique side view diagram of the lower assembly.

Turning now to FIG. 11, shown is a top oblique view of the lower assembly 1100. The lower assembly 1100 is comprised of the lower assembly base 250, a wick 240 and a heating coil 1110. In one embodiment, the lower assembly base 250 is made from a semi-flexible material such as silicone. On the distal side of the lower assembly base 250 is shown the lower assembly air channel delimiter 1130. The lower assembly air channel delimiter 1130 separates the lower assembly residue basin 1140 from the lower assembly air channel 1120.

Figure 12:
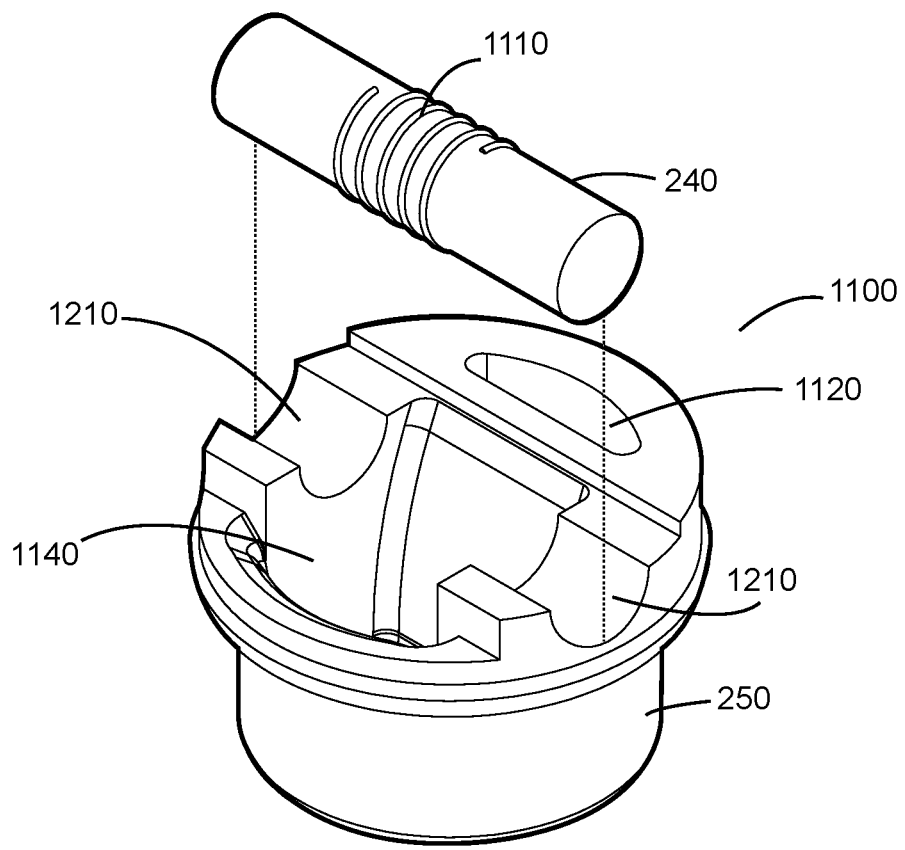
FIG. 12 is an oblique side view exploded diagram of the lower assembly.

FIG. 12 is an exploded view of the lower assembly 1100 in which the wick receptacles 1210 can be seen on either side of the lower assembly base 250. The legs of the heating coil 1110 (not shown) extend down through the lower assembly residue basin 1140 for connection to the battery assembly attachment. In one embodiment, the heating coil 1110 is wrapped around the wick 240 five times to provide sufficient energy to the wick to vaporize the oil. The wick 240 comprising a ceramic rod sits on top of the wick receptacles 1210. The nickel cadmium wire comprising the heating coil 1110 wraps around the wick 240 with the ends, referred to as legs (not shown), extending down through the lower assembly 1100 such that they contact the battery attachment assembly. The base of the lower assembly base 250 is made of silicone, and the legs can be pushed through the silicone at the lower assembly residue basin floor to come into contact with the battery assembly. This provides a tight seal around the legs. The legs of the heating coil 1110 pass go through the lower assembly residue basin floor, and there are no holes tooled in the silicone; the legs are pushed through the silicone when assembled. This prevents leakage from the lower assembly residue basin 1210. This also serves to secure the wick 240 to the lower assembly base 250 and conduct electricity to the heating coil 1110 from the battery which is in contact with the battery attachment assembly. The proximal end of the wire extends up from the proximal side of the battery attachment assembly, through the lower assembly base 250 and wraps 5 times around the wick 240, and then extends down through the distal side of the lower assembly base 250 and contacts the distal side of the battery attachment assembly. The lower assembly 1100 also has an air channel on the distal side.

Figure 13:
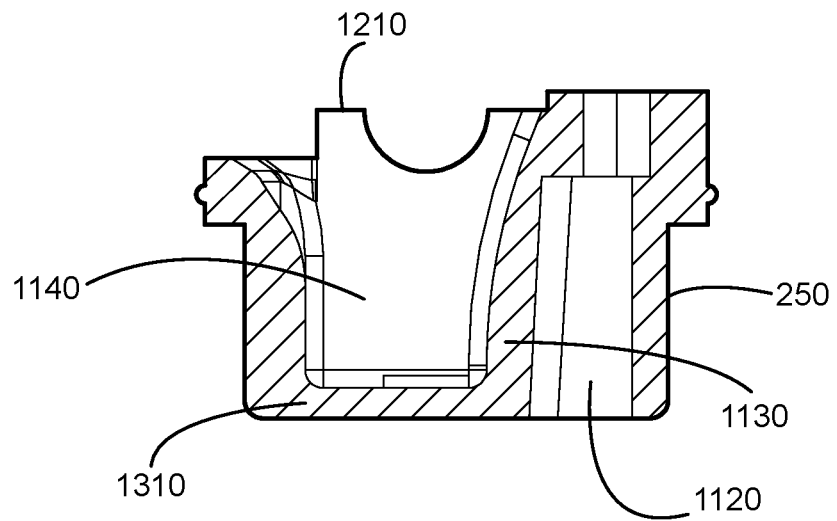
FIG. 13 is a side view cutaway diagram of the lower assembly base.

Turning now to FIG. 13, shown is a side cutaway view of the lower assembly base 250. From this perspective, it can be seen that the lower assembly air channel 1120 flows through the lower assembly base and the lower assembly residue basin 1140 is separated from the lower assembly air channel 1120 by the lower assembly air channel delimiter 1130. The lower assembly residue basin floor 1310 separates the lower assembly residue basin 1140 from the battery attachment assembly underneath. In one embodiment, the distance from the lowest point in the wick receptacle 1210 to the lower assembly residue basin floor is between 3 mm to 5 mm.

Figure 14:
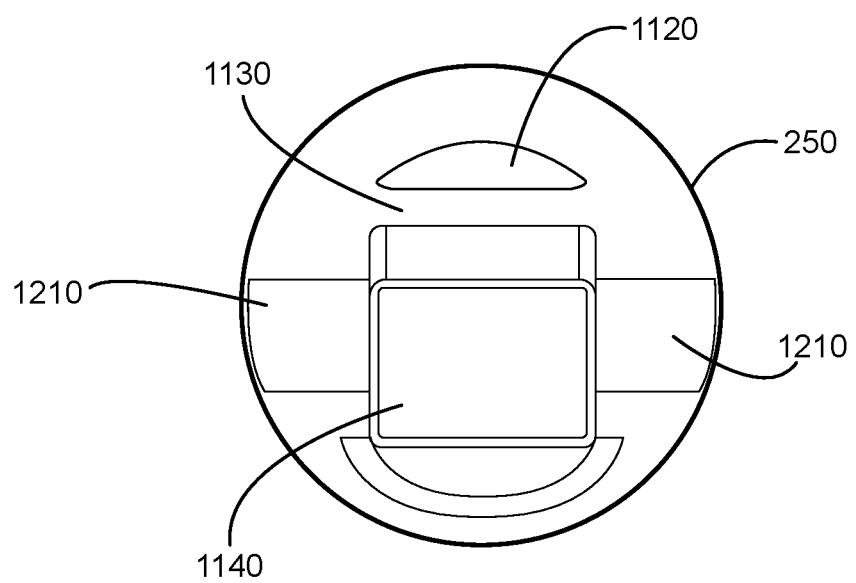
FIG. 14 is a top view diagram of the lower assembly base.

Turning now to FIG. 14, shown is a top view of the lower assembly base 250. From the top view, the lower assembly base 250 is circular in shape and fits snugly in the housing below the upper assembly. The lower assembly base 250 is cylindrical in shape and is generally hollow. Extending from the bottom of the upper assembly base 250 is a lower assembly air channel delimiter 1130. The lower assembly air channel delimiter 1130 is affixed offset from the center of the lower assembly base 250 such that the lower assembly air channel 1120 delimited thereby is a minority of the area circumscribed and the bottom of that area is open and provides a lower assembly air channel 1120. The area circumscribed by the walls of the lower assembly base 250 and lower assembly air channel delimiter 1130 circumscribe the lower assembly residue basin 1140. The wick receptacles 1210 provide support for the wick which extends across and over the lower assembly residue basin 1140. When the lower assembly base 250 is inserted into the housing, it is positioned such that the wick is seated in the upper assembly wick retainers 1210 and the lower assembly air channel is on the opposite side as the vapor channel.

Figure 15:
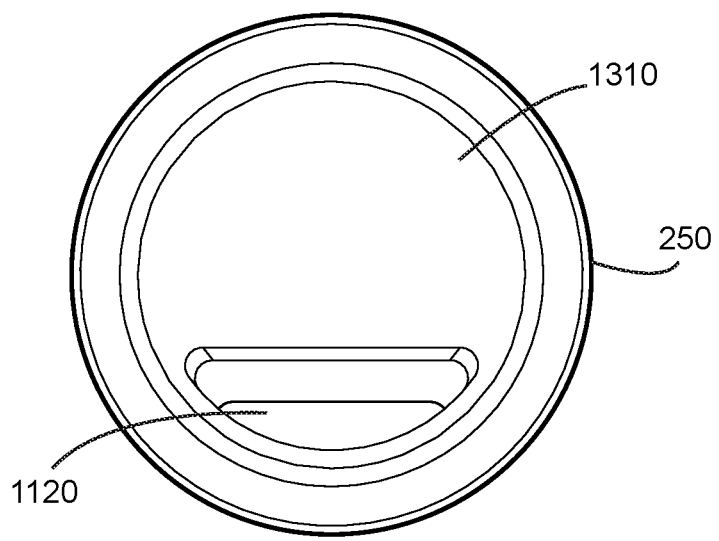
FIG. 15 is a bottom view diagram of the lower assembly base.

Turning now to FIG. 15, shown is a bottom view of the lower assembly base 250. From the bottom, the majority of the area circumscribed comprises the lower assembly residue basin floor 1310. In one embodiment, a heating coil is wrapped around the wick with each end extending down through the lower assembly residue basin floor 1310 where it is electrically connected to the battery attachment assembly.

Figure 16:
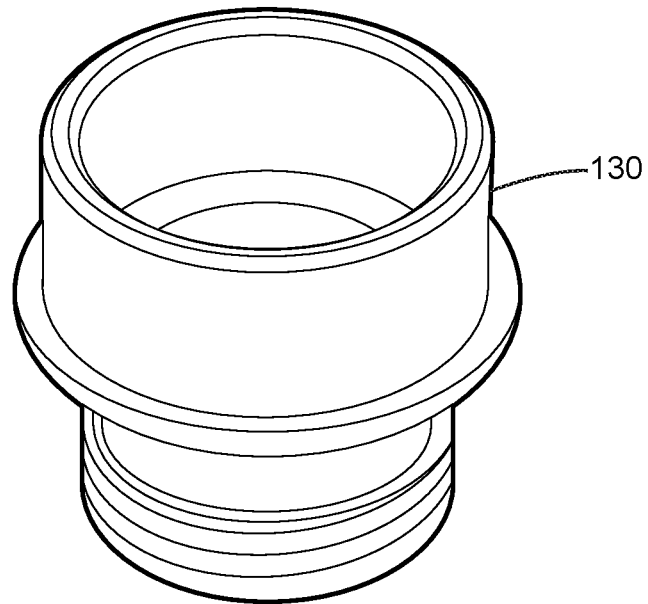
FIG. 16 is an oblique side view diagram of the battery attachment assembly.

Turning now to FIG. 16, shown is the battery attachment assembly 130 which is cylindrical in shape and partially fits in the housing 120 securely under the lower assembly 1100 creating a sealed cartridge. It serves as the interface between the lower assembly 1100 and a battery or power source.

Figure 17:
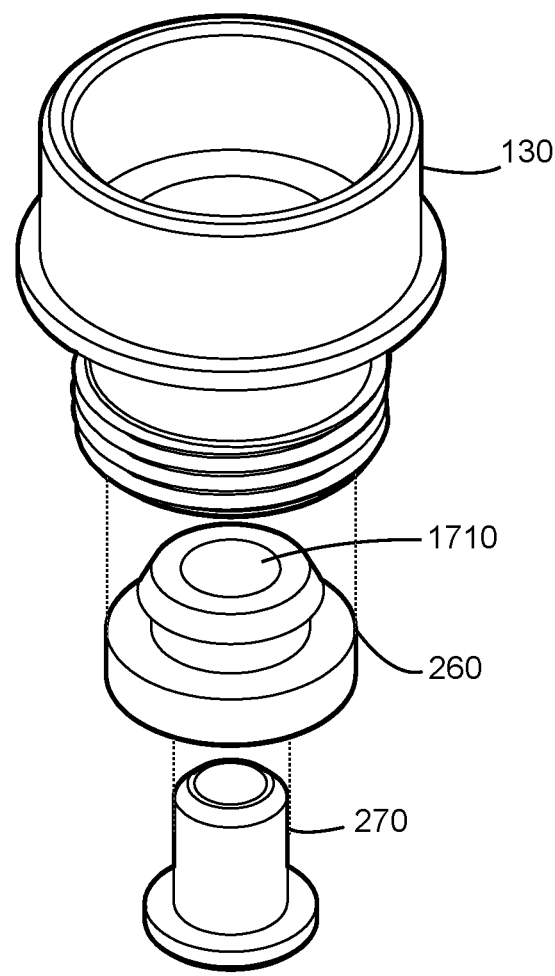
FIG. 17 is an oblique side view exploded diagram of the battery attachment assembly.

Turning now to FIG. 17, shown is the battery attachment assembly 130 from an exploded top oblique view. The battery attachment assembly has a retainer 260, a center pin 270, and a second air intake vent 1710 that runs up the center through the center pin 270 and retainer 260. The legs of the heating coil are held in place between the battery attachment assembly 130 and retainer 260 by pressure from the retainer 260. A battery attachment assembly comprising a battery housing and a battery may be secured to the battery attachment assembly, thereby completing the vaporizer. The battery is positioned inside the battery housing such that it comes into contact with the center pin, thereby providing electrical power to the heating coil.

Figure 18:
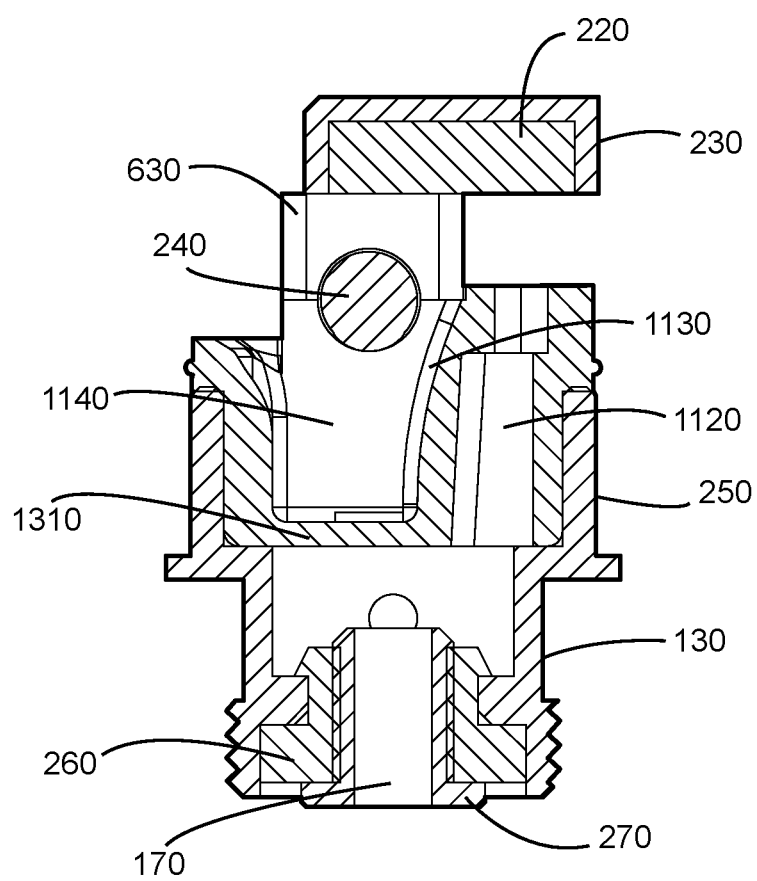
FIG. 18 is a side view cutaway diagram of the upper assembly, lower assembly and battery attachment assembly.

Turning now to FIG. 18, shown is side cutaway of the assembled upper assembly, lower assembly 1100 and battery attachment assembly 130.

Figure 19:
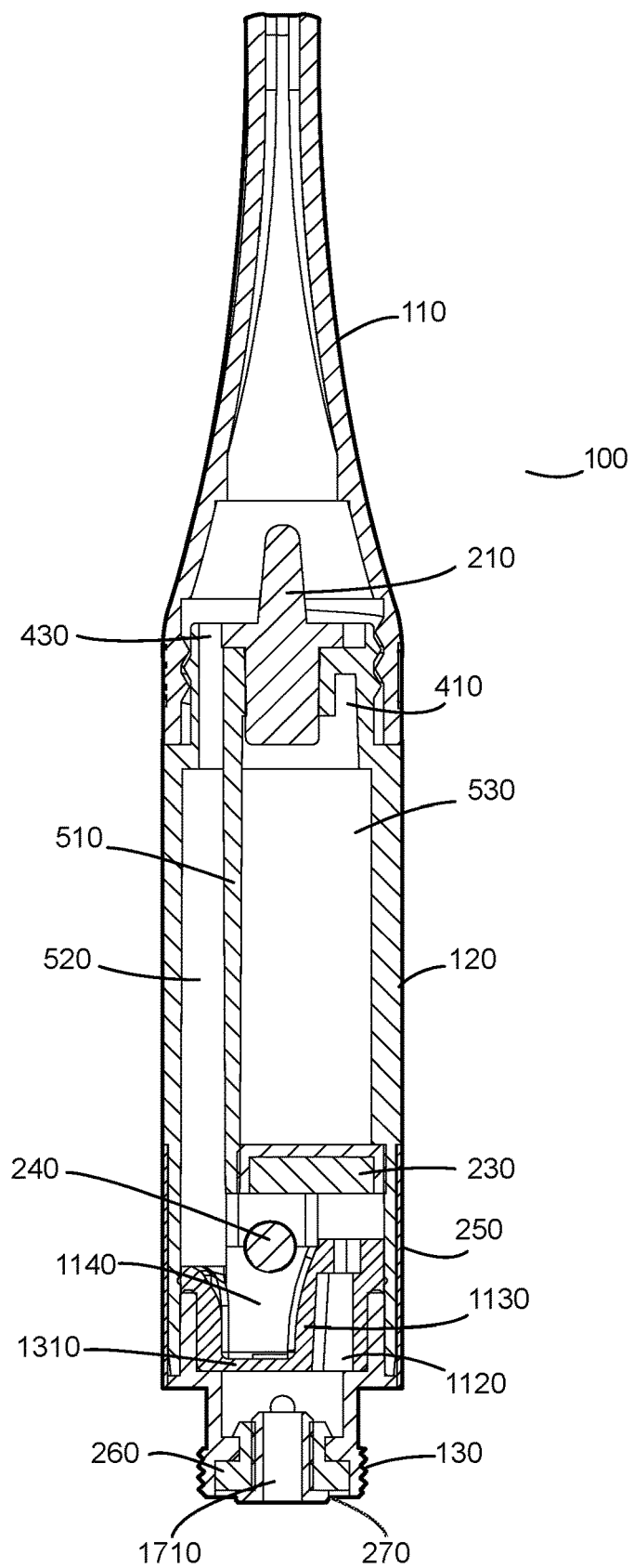
FIG. 19 is a side view cutaway diagram of the vaporizer cartridge.

Turning now to FIG. 19, shown is a side cutaway of the assembled vaporizer cartridge. When a user inhales through the mouthpiece 110, negative pressure is created within the vaporizer cartridge 100. The negative pressure causes air to be pulled through the battery where it triggers a sensor that causes a battery attached via the battery attachment assembly 130 to provide electrical power to the heating coil 240, which heats the wick 240. When the wick 240 is heated, heat is released up through the upper assembly oil feeder tubes. The oil in proximity to the upper assembly oil feeder tubes becomes less viscous, and flows down through the upper assembly oil feeder tubes into the lower assembly residue basin 1140 where it is vaporized by the heat generated from the wick 240. The lower assembly residue basin 1140 is deep enough so that it can capture oil that have previously leaked through the upper assembly oil feeder tubes, but is also shallow enough so that any captured oil will be vaporized on the next heat cycle of the wick. In one embodiment of the present invention, the distance from the bottom of the wick 240 to the lower assembly residue basin floor This advantageously collects enough residue to vaporize without clogging. The negative pressure also causes air to be pulled in through the air intake vent and second air intake vent 1710 in the battery attachment assembly 130, up through the lower assembly air channel 1120, across the wick 240 and over the lower assembly residue basin 1140, thereby pulling the vapor up past the upper assembly, through the vapor channel 520, out of the vapor outflow vent 430 of the housing 120 and through the mouthpiece 110 to the user.

It should be further understood that the examples and embodiments pertaining to the systems and methods disclosed herein are not meant to limit the possible implementations of the present technology. Further, although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A cartridge for a vaporization device, said cartridge comprising:
an elongate housing;
a reservoir configured to hold vaporizable material within said housing;
a vapor assembly situated below said reservoir within said housing, said vapor assembly comprising:
a ceramic wick,
a heating coil wrapped around said ceramic wick wherein each end of said heating coil is configured to contact a battery attachment assembly thereby completing a circuit when said cartridge is inserted into said vaporization device, and
a residue basin situated below said ceramic wick configured to hold vaporizable material residue;
wherein said vapor assembly comprises an upper assembly and a lower assembly, wherein said upper assembly comprises an upper assembly base, at least one oil vent, at least one oil feeder tube, and two wick retainers, and wherein said lower assembly comprises a lower assembly base, two wick receptacles, a lower assembly air channel delimiter, and said residue basin, and whereby said upper assembly is situated on top of said lower assembly such that said ceramic wick is held in place by said wick retainers and said wick receptacles;
an upper assembly support made of material that is more rigid than said upper assembly is situated in a depression on top of said upper assembly, thereby providing structural support for, and tighter seal of, said upper assembly within said housing.

2. The cartridge of claim 1, further comprising a lower air channel extending from a bottom distal side of said housing up to said ceramic wick, an upper air channel extending from a top proximal side of said housing down to said ceramic wick, and a cross air channel extending from a top of said lower air channel across said ceramic wick and said residue basin to a bottom of said upper air channel.

3. The cartridge of claim 1 wherein said heating coil is operable to heat said ceramic wick to a vaporization temperature.

4. The cartridge of claim 1 wherein a floor of said residue basin is situated between three millimeters and five millimeters below said ceramic wick.

5. The cartridge of claim 1 wherein said residue basin is made of silicone.

6. The cartridge of claim 1 wherein said upper assembly and said lower assembly are made of silicone.

7. The cartridge of claim 1 wherein said upper assembly support is made of plastic.

8. A vaporizer, said vaporizer comprising:
a mouthpiece;
a cartridge, wherein said mouthpiece is connected to a top end of said cartridge, said cartridge comprising:
an elongate housing;
a reservoir configured to hold vaporizable material within said housing;
a vapor assembly situated below said reservoir within said housing, said vapor assembly comprising:
a ceramic wick,
a heating coil wrapped around said ceramic wick wherein each end of said heating coil is configured to contact a battery attachment assembly thereby completing a circuit when said cartridge is inserted into said vaporization device, and
a residue basin situated below said ceramic wick configured to hold vaporizable material residue;
a battery component, wherein said battery component is electrically connected to a bottom end of said cartridge;

wherein said vapor assembly comprises an upper assembly and a lower assembly, wherein said upper assembly comprises an upper assembly base, at least one oil vent, at least one oil feeder tube, and two wick retainers, and wherein said lower assembly comprises a lower assembly base, two wick receptacles, a lower assembly air channel delimiter, and said residue basin, and whereby said upper assembly is situated on top of said lower assembly such that said ceramic wick is held in place by said wick retainers and said wick receptacles; and an upper assembly support made of material that is more rigid than said upper assembly is situated in a depression on top of said upper assembly, thereby providing structural support for, and tighter seal of, said upper assembly within said housing.

9. The vaporizer of claim 8, further comprising a lower air channel extending from a bottom distal side of said housing up to said ceramic wick, an upper air channel extending from a top proximal side of said housing down to said ceramic wick, and a cross air channel extending from a top of said lower air channel across said ceramic wick to a bottom of said upper air channel.

10. The vaporizer of claim 8 wherein said heating coil is operable to heat said ceramic wick to a vaporization temperature.

11. The vaporizer of claim 8 wherein a floor of said residue basin is situated between three millimeters and 5 millimeters below said ceramic wick.

12. The vaporizer of claim 8 wherein said residue basin is made of silicone.

13. The vaporizer of claim 8 wherein said upper assembly and said lower assembly are made of silicone.

14. The vaporizer of claim 8 wherein said upper assembly support is made of plastic.

* * * * *